US00PP37202P2

(12) United States Plant Patent
Koot

(10) Patent No.: US PP37,202 P2
(45) Date of Patent: Jan. 6, 2026

(54) ***PETUNIA* PLANT NAMED 'Dopetsurspabluvei'**

(50) Latin Name: ***Petunia* X *hybrida***
Varietal Denomination: Dopetsurspabluvei

(71) Applicant: DUMMEN GROUP B.V., De Lier (NL)

(72) Inventor: Arjan Koot, Oeffelt (NL)

(73) Assignee: Dünnen Group B.V., De Lier (NL)

( * ) Notice: Subject to any disclaimer, the term of this patent is extended or adjusted under 35 U.S.C. 154(b) by 0 days.

(21) Appl. No.: 19/054,438

(22) Filed: Feb. 14, 2025

(51) Int. Cl.
*A01H 5/02* (2018.01)
*A01H 6/82* (2018.01)

(52) U.S. Cl.
USPC ..... Plt./356.2
CPC ..... *A01H 6/824* (2018.05); *A01H 5/02* (2013.01)

(58) Field of Classification Search
USPC ..... Plt./356.2, 356.13, 356.1
CPC . A01H 5/02; A01H 5/00; A01H 6/824; A01H 6/82
See application file for complete search history.

(56) References Cited

PUBLICATIONS

BFG Supply Knox Nursery Inc. 2024-2025 Program, retrieved on Apr. 30, 2025 at https://www.bfgsupply.com/media/10423/2025-knox-nursery-product-program.pdf, 5 pp. (Year: 2025).*
Dummen Orange retrieved on Apr. 30, 2025 at https://na.dummenorange.com/app/en/products/usa/petunia/surprise-sparkle-blue-vein-(intrinsa)/PAT_38416, one page. (Year: 2025).*

* cited by examiner

*Primary Examiner* — June Hwu
(74) *Attorney, Agent, or Firm* — C. Anne Whealy

(57) ABSTRACT

A new and distinct cultivar of *Petunia* plant named 'Dopetsurspabluvei', characterized by its semi-upright and uniformly mounding plant habit; relatively moderately vigorous growth habit and moderate growth rate; freely branching habit; early and freely flowering habit; large light purple-colored flowers with large dark purple to dark violet-colored centers with occasional and random small white-colored blotches; good container and garden performance; and resistance to Tobacco Mosaic Virus.

1 Drawing Sheet

Botanical designation: *Petunia* X *hybrida.*
Cultivar denomination: 'DOPETSURSPABLUVEI'.

BACKGROUND OF THE INVENTION

The present invention relates to a new and distinct cultivar of *Petunia* plant, botanically known as *Petunia* X *hybrida* and hereinafter referred to by the name 'Dopetsurspabluvei'.

The new *Petunia* plant is a product of a planned breeding program conducted by the Inventor in Rheinberg, Germany. The objective of the breeding program is to create new compact, freely branching and early-flowering *Petunia* plants with numerous attractive flowers.

The new *Petunia* plant originated from a cross-pollination made by the Inventor in July 2022 in Rheinberg, Germany of a proprietary selection of *Petunia* X *hybrida* identified as code number TT22-K0745, not patented, as the female, or seed, parent with a proprietary selection of *Petunia* X *hybrida* identified as code number TT22-K0401, not patented, as the male, or pollen, parent. The new *Petunia* plant was discovered and selected by the Inventor as a single flowering plant from within the progeny of the stated cross-pollination in a controlled greenhouse environment in Rheinberg, Germany in April 2023.

Asexual reproduction of the new *Petunia* plant by terminal vegetative cuttings in a controlled greenhouse environment in Rheinberg, Germany since April 2023 has shown that the unique features of this new *Petunia* plant are stable and reproduced true to type in successive generations.

SUMMARY OF THE INVENTION

Plants of the new *Petunia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dopetsurspabluvei'. These characteristics in combination distinguish 'Dopetsurspabluvei' as a new and distinct *Petunia* plant:

1. Semi-upright and uniformly mounding plant habit.
2. Relatively moderately vigorous growth habit and moderate growth rate.
3. Freely branching habit.
4. Early and freely flowering habit.
5. Large light purple-colored flowers with large dark purple to dark violet-colored centers with occasional and random small white-colored blotches.
6. Good container and garden performance.
7. Resistant to Tobacco Mosaic Virus.

Plants of the new *Petunia* can be compared to plants of the female parent selection. In side-by-side comparisons, plants of the new *Petunia* differ primarily from plants of the female parent selection in the following characteristics:

1. Plants of the new *Petunia* are not as vigorous as plants of the female parent selection.
2. Flowers of plants of the new *Petunia* are light purple in color with large dark purple to dark violet-colored centers with occasional and random small white-colored blotches whereas flowers of plants of the female parent selection are solid blue in color.
3. Flowers of plants of the new *Petunia* resist fading better than flowers of plants of the female parent selection.

Plants of the new *Petunia* can be compared to plants of the male parent selection. In side-by-side comparisons, plants of the new *Petunia* differ primarily from plants of the male parent selection in the following characteristics:

1. Plants of the new *Petunia* are more freely branching than plants of the male parent selection.
2. Flowers of plants of the new *Petunia* are light purple in color with large dark purple to dark violet-colored centers with occasional and random small white-colored blotches whereas flowers of plants of the male parent selection are purple in color with random white-colored blotches.

Plants of the new *Petunia* can be compared to plants of *Petunia hybrida* 'KLEPH15313', disclosed in U.S. Plant Pat. No. 27,237. In side-by-side comparisons, plants of the new *Petunia* and 'KLEPH15313' differ primarily in the following characteristics:

1. Plants of the new *Petunia* are not as vigorous as plants of 'KLEPH15313'.
2. Plants of the new *Petunia* have larger leaves than plants of 'KLEPH15313'.
3. Plants of the new *Petunia* have larger flowers than plants of 'KLEPH15313'.
4. Flowers of plants of the new *Petunia* are light purple in color with large dark purple to dark violet-colored centers with occasional and random small white-colored blotches whereas flowers of plants of 'KLEPH15313' are purple in color with random white-colored blotches.
5. Plants of the new *Petunia* are resistant to Tobacco Mosaic Virus whereas plants of 'KLEPH15313' are not resistant to Tobacco Mosaic Virus.

BRIEF DESCRIPTION OF THE PHOTOGRAPH

The accompanying colored photograph illustrates the overall appearance of the new *Petunia* plant showing the colors as true as it is reasonably possible to obtain in colored reproductions of this type. Colors in the photograph may differ slightly from the color values cited in the detailed botanical description which accurately describe the colors of the new *Petunia* plant.

The photograph is a side perspective view of a typical flowering plant of 'Dopetsurspabluvei' grown in a container.

DETAILED BOTANICAL DESCRIPTION

The aforementioned photograph and following observations, measurements and values describe plants grown during the spring and summer in 22-cm containers in a glass-covered greenhouse in Rheinberg, Germany and under cultural practices typical of commercial *Petunia* production. During the production of the plants, day and night temperatures averaged 18° C. and light levels averaged 4,500 lux. Plants were twelve weeks from planting rooted young plants when the photograph was taken and 25 weeks from planting rooted young plants when the description was taken. In the following description, color references are made to The Royal Horticultural Society Colour Chart, Fifth Edition, except where general terms of ordinary dictionary significance are used.

Botanical classification: *Petunia* X *hybrida* 'Dopetsurspabluvei'.

Parentage:

*Female, or seed, parent.*—Proprietary selection of *Petunia* X *hybrida* identified as code number TT22-K0745, not patented.

*Male, or pollen, parent.*—Proprietary selection of *Petunia* X *hybrida* identified as code number TT22-K0401, not patented.

Propagation:

*Type.*—By terminal vegetative cuttings.

*Time to initiate roots, summer.*—About five days at temperatures about 20° C.

*Time to initiate roots, winter.*—About seven days at temperatures about 20° C.

*Time to produce a rooted young plant, summer.*—About three weeks at temperatures about 20° C.

*Time to produce a rooted young plant, winter.*—About four weeks at temperatures about 20° C.

*Root description.*—Fine, fibrous; close to 155B in color, actual color of the roots is dependent on substrate composition, water quality, fertilizers, substrate temperature and age of roots.

*Rooting habit.*—Freely branching; dense.

Plant description:

*Plant and growth habit.*—Semi-upright and uniformly mounding plant habit; freely branching habit with about eight to ten primary lateral branches each with about three to five secondary branches developing after pinching; relatively moderately vigorous growth habit and moderate growth rate.

*Plant height, soil level to top of foliar plane.*—About 22 cm.

*Plant height, soil level to top of floral plane.*—About 24 cm.

*Plant diameter.*—About 56.3 cm.

Lateral branch description:

*Length.*—About 32 cm.

*Diameter.*—About 7 mm.

*Internode length.*—About 1.6 cm.

*Strength.*—Moderately strong.

*Aspect.*—Initially upright to somewhat outwardly spreading to eventually trailing.

*Texture and luster.*—Pubescent; semi-glossy.

*Color, developing.*—Close to 143C.

*Color, developed.*—Close to 144A.

Leaf description:

*Arrangement.*—Before flowering, alternate; after flowering, opposite; simple.

*Length.*—About 4.4 cm.

*Width.*—About 2.3 cm.

*Shape.*—Spatulate.

*Apex.*—Obtuse.

*Base.*—Attenuate.

*Margin.*—Entire.

*Texture and luster, upper and lower surfaces.*—Pubescent; leathery; semi-glossy.

*Venation pattern.*—Pinnate; arcuate.

*Color*.—Developing leaves, upper surface: Close to 143A. Developing leaves, lower surface: Close to 138A. Fully expanded leaves, upper surface: Close to 137A; venation, close to 144A. Fully expanded leaves, lower surface: Close to 138B; venation, close to 143C.

*Petioles*.—Length: About 1 cm. Diameter: About 3.4 mm. Strength: Moderately strong; firm. Texture and luster, upper and lower surfaces: Smooth, glabrous; matte. Color, upper surface: Close to 144A. Color, lower surface: Close to 143C.

Flower description:

*Flower type and flowering habit*.—Single salverform flowers arising from leaf axils; freely flowering habit with usually about 276 flowers and flower buds developing per plant during the flowering season; flowers face mostly upright to somewhat outwardly.

*Fragrance*.—None detected.

*Natural flowering season*.—Plants flower continuously during the spring and summer in Germany; early flowering habit, plants typically beginning flowering about nine weeks after planting.

*Flower longevity*.—Depending on temperature and light levels, individual flowers last about two to six days on the plant; flowers persistent.

*Flower buds*.—Length: About 3.7 cm. Diameter: About 6.6 mm. Shape: Ovoid. Texture and luster: Rippled; semi-glossy. Color: Close to 144D and N77C.

*Flower diameter*.—About 5.9 cm by 6.5 cm.

*Flower depth* (*height*).—About 5.2 cm.

*Flower throat diameter*.—About 1 cm.

*Flower tube length*.—About 2.7 cm.

*Flower tube diameter, proximally*.—About 7.8 mm.

*Corolla*.—Arrangement: Five petals fused at the base and opening into a flared trumpet; moderately lobed. Petal lobe length (from throat): About 3.2 cm. Petal lobe width: About 3 cm. Petal shape: Roughly spatulate. Petal apex: Obtuse. Petal margin: Entire; slightly undulate. Petal texture and luster, upper and lower surfaces: Rugose, glabrous; semi-glossy. Throat texture and luster: Rugose, glabrous; semi-glossy. Tube texture and luster: Rugose, glabrous; semi-glossy. Color: Petal lobe, when opening and fully opened, upper surface: Close to 85A, 85B and 85C; centers, close to 83C, N92D and N186A; occasional and random small blotches, close to NN155C; venation, moderately conspicuous and close to N186A; color becoming closer to N186A with subsequent development. Petal lobe, when opening and fully opened, lower surface: Close to N187A, 79C and N82D; occasional and random small blotches, close to 155C; venation, moderately conspicuous and close to N187A; color becoming closer to N187A with subsequent development. Flower throat: Close to N186A; venation, close to N186A. Flower tube: Close to N187A; venation, close to N187A.

*Sepals*.—Arrangement: Five sepals fused at the base forming a tubular star-shaped calyx. Length: About 1.7 cm. Diameter: About 7 mm. Shape: Oblong. Apex: Rounded. Base: Decurrent. Margin: Entire. Texture and luster, upper and lower surfaces: Smooth, glabrous; semi-glossy. Color: When opening, upper surface: Close to 137B. When opening, lower surface: Close to 137D. Fully opened, upper surface: Close to 137C. Fully opened, lower surface: Close to 137D.

*Peduncles*.—Length: About 4.1 cm. Diameter: About 2 mm. Strength: Moderately strong. Texture and luster: Smooth, glabrous; semi-glossy. Color: Close to 137C.

*Reproductive organs*.—Stamens: Quantity per flower: Five. Filament length: About 1.1 cm. Filament color: Close to 155C. Anther size: About 1.2 mm by 2 mm. Anther shape: Ovate. Anther color: Close to 162B. Pollen amount: Abundant. Pollen color: Close to 97B. Pistils: Quantity per flower: One. Pistil length: About 2.3 cm. Style length: About 1.9 cm. Style color: Close to 79A and 145D. Stigma diameter: About 2 mm. Stigma shape: Rounded. Stigma color: Close to N137A. Ovary color: Close to 144C. Fruits: Quantity produced per plant: About 20 during the flowering season. Length: About 4 mm. Diameter: About 3 mm. Texture: Smooth, glabrous. Color: Close to 143C. Seeds: Quantity per flower: About 28. Length: About 0.8 mm. Diameter: About 0.8 mm. Texture: Smooth, glabrous. Color: Close to 161B.

Garden performance: Plants of the new *Petunia* have been observed to have good garden performance and tolerate wind, rain, temperatures ranging from about 3° C. to about 28° C. and to be suitable for USDA Hardiness Zone 11.

Pathogen resistance: Plants of the new *Petunia* have been observed to be resistant to Tobacco Mosaic Virus. To date, plants of the new *Petunia* have not been observed to be resistant to other pathogens common to *Petunia* plants.

It is claimed:

1. A new and distinct *Petunia* plant named 'Dopetsursp-abluvei' as herein illustrated and described.

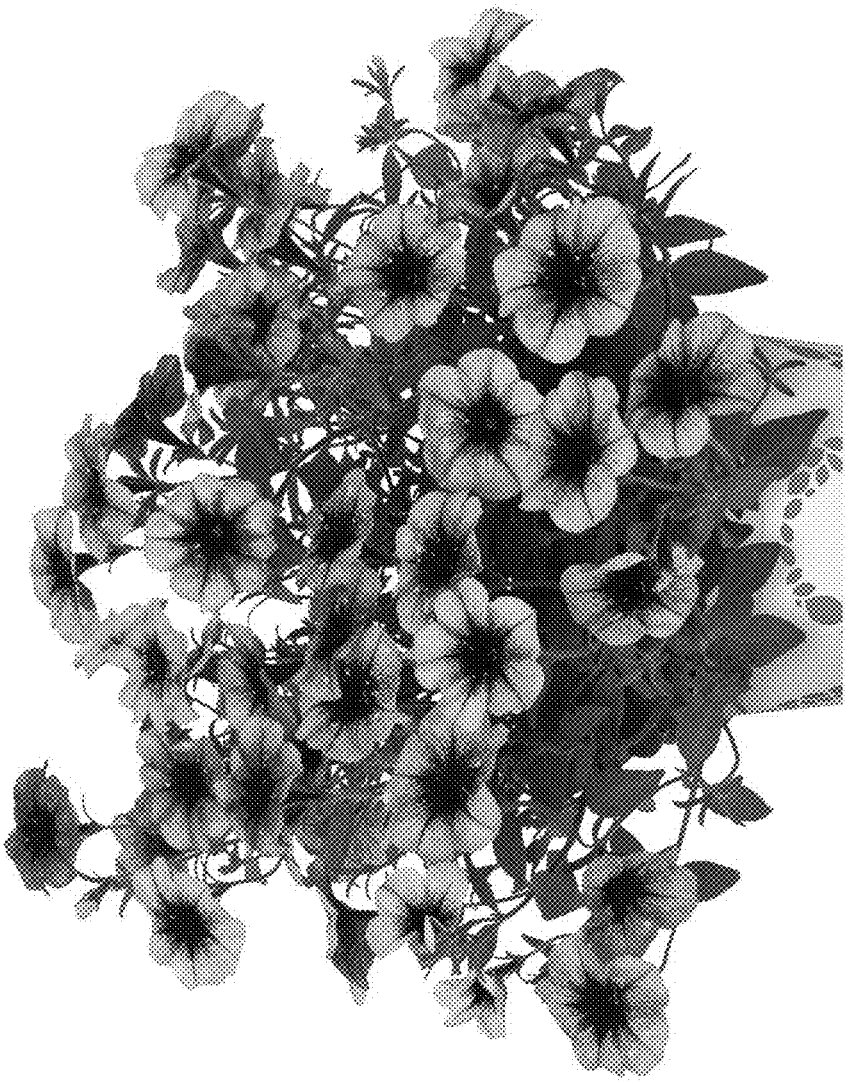

* * * * *